(12) United States Patent
Yoda

(10) Patent No.: US 10,531,854 B2
(45) Date of Patent: Jan. 14, 2020

(54) X-RAY CT APPARATUS

(71) Applicant: TOSHIBA MEDICAL SYSTEMS CORPORATION, Otawara-shi (JP)

(72) Inventor: Takahiro Yoda, Nasushiobara (JP)

(73) Assignee: CANON MEDICAL SYSTEMS CORPORATION, Otawara-shi (JP)

(*) Notice: Subject to any disclaimer, the term of this patent is extended or adjusted under 35 U.S.C. 154(b) by 541 days.

(21) Appl. No.: 15/365,101

(22) Filed: Nov. 30, 2016

(65) Prior Publication Data

US 2017/0150936 A1   Jun. 1, 2017

(30) Foreign Application Priority Data

Dec. 1, 2015   (JP) .................................. 2015-234718
Nov. 29, 2016  (JP) .................................. 2016-231845

(51) Int. Cl.
*A61B 6/03*      (2006.01)
*G01N 23/04*     (2018.01)
(Continued)

(52) U.S. Cl.
CPC ............ *A61B 6/5235* (2013.01); *A61B 6/032* (2013.01); *A61B 6/4233* (2013.01); *A61B 6/482* (2013.01);
(Continued)

(58) Field of Classification Search
CPC ........... A61B 6/03; A61B 6/032; A61B 6/482; A61B 6/5205; G01N 23/04; G01N 23/046; G01N 23/087; G01N 23/10; G06T 11/005
See application file for complete search history.

(56) References Cited

U.S. PATENT DOCUMENTS 5,570,403 A    10/1996  Yamazaki et al.
9,585,626 B2 *  3/2017  Gao ........................ A61B 6/032
(Continued)

FOREIGN PATENT DOCUMENTS

JP         6-296607      10/1994
JP         2009-261942   11/2009
JP         2010-246958   11/2010

*Primary Examiner* — Thomas R Artman
(74) *Attorney, Agent, or Firm* — Oblon, McClelland, Maier & Neustadt, L.L.P.

(57) ABSTRACT

An X-ray CT apparatus includes processing circuitry. The circuitry controls a voltage generator during non-helical scan to switch tube voltage, thereby causing an imaging to be performed separately with X-rays of a first energy and X-rays of a second energy. The circuitry generates first and second projection data sets, respectively. The circuitry performs image reconstruction based on the first and second projection data sets respectively, thereby generating first and second images respectively. The circuitry performs alignment processing to align the second image with the first image. The circuitry generates a third projection data set based on a processing result of the alignment processing. The circuitry performs transformation processing to transform the second and third projection data sets into projection data sets corresponding to reference materials. The circuitry performs image reconstruction based on the projection data sets after the transformation processing, thereby generating reference material images corresponding to reference materials.

7 Claims, 14 Drawing Sheets

(51) Int. Cl.
  *A61B 6/00*    (2006.01)
  *G01N 23/046*  (2018.01)
  *G06T 11/00*   (2006.01)

(52) U.S. Cl.
  CPC ............. *A61B 6/54* (2013.01); *G01N 23/046* (2013.01); *G06T 11/005* (2013.01)

(56) References Cited

U.S. PATENT DOCUMENTS

| | | | |
|---|---|---|---|
| 9,977,140 B2 * | 5/2018 | Wang | A61B 6/032 |
| 10,045,743 B2 * | 8/2018 | Grant | A61B 6/5205 |
| 10,111,638 B2 * | 10/2018 | Qiulin | A61B 6/5205 |
| 10,255,697 B2 * | 4/2019 | Homann | G06T 11/008 |
| 2009/0262997 A1 | 10/2009 | Zou et al. | |
| 2016/0166221 A1 * | 6/2016 | Gao | A61B 6/032 |
| | | | 378/5 |
| 2016/0202364 A1 * | 7/2016 | Wang | A61B 6/032 |
| | | | 378/5 |
| 2016/0302751 A1 * | 10/2016 | Grant | A61B 6/5205 |
| 2017/0150936 A1 * | 6/2017 | Yoda | A61B 6/5235 |
| 2017/0316588 A1 * | 11/2017 | Homann | G06T 11/008 |
| 2017/0340304 A1 * | 11/2017 | Qiulin | A61B 6/5205 |
| 2017/0352166 A1 * | 12/2017 | Raupach | A61B 6/032 |

\* cited by examiner

X-RAY CT APPARATUS

CROSS-REFERENCE TO RELATED APPLICATION

This application is based upon and claims the benefit of priority from Japanese Patent Application No. 2015-234718, filed on Dec. 1, 2015, and Japanese Patent Application No. 2016-231845, filed on Nov. 29, 2016, the entire contents of each of which are incorporated herein by reference.

FIELD

An embodiment as an aspect of the present invention relates to an X-ray CT (computed tomography) apparatus.

BACKGROUND

X-ray CT apparatuses, which provide information on an object by means of images based on the intensity of X-rays transmitted through the object, have been playing an important role in various medical practices, including diagnostics and treatments of diseases, and surgical planning.

In recent years, the X-ray CT apparatus utilizes a technique called Dual Energy Scan. The Dual Energy Scan is a technique to generate image data sets by performing an imaging using two different kinds of tube voltages.

As conventional reconstruction methods available when the Dual Energy Scan is used, two types of construction methods exist: dual energy reconstruction based on image data sets, and dual energy reconstruction based on projection data sets. The dual energy reconstruction based on the image data sets generates the image data sets from the projection data sets obtained at a high tube voltage and a low tube voltage respectively, and thereafter performs decomposition calculation on the image data sets to generate reference-material image data sets.

On the other hand, the dual energy reconstruction performs, in a non-helical scan, decomposition calculation respectively on a pair (Low-kV and High-kV) of actual measured projection data sets at same slice center position, and thereafter generates reference-material image data sets.

Thus, it is an objective of the present invention to provide an X-ray CT apparatus which enables high precision dual energy reconstruction based on the projection data sets.

BRIEF DESCRIPTION OF THE DRAWINGS

In accompanying drawings.

Figure 9A:
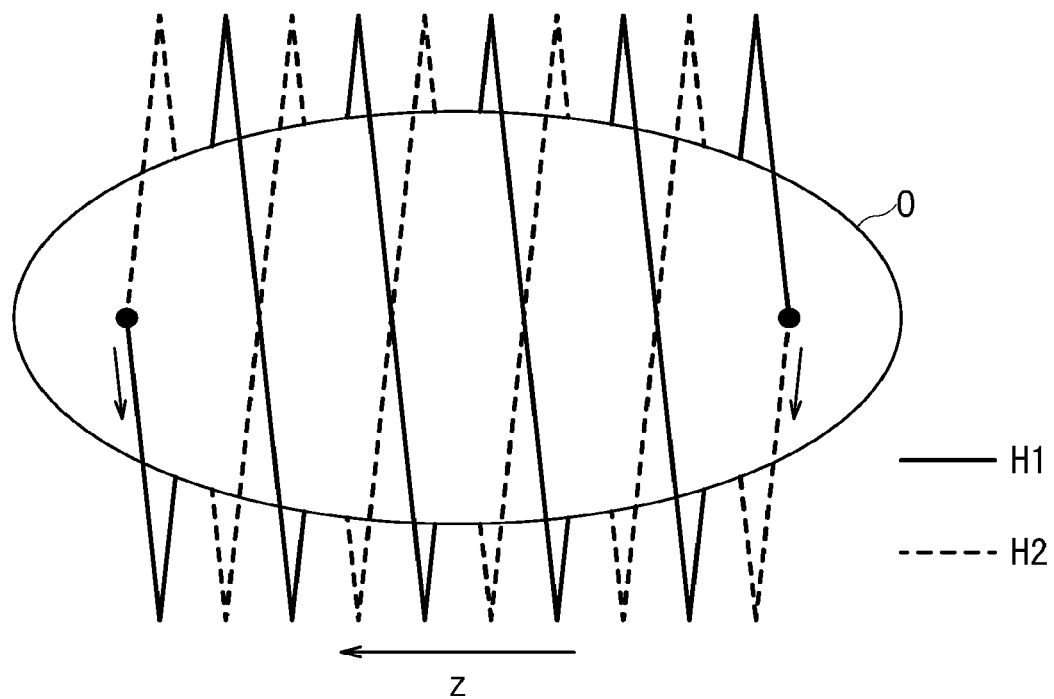
Figure 9B:
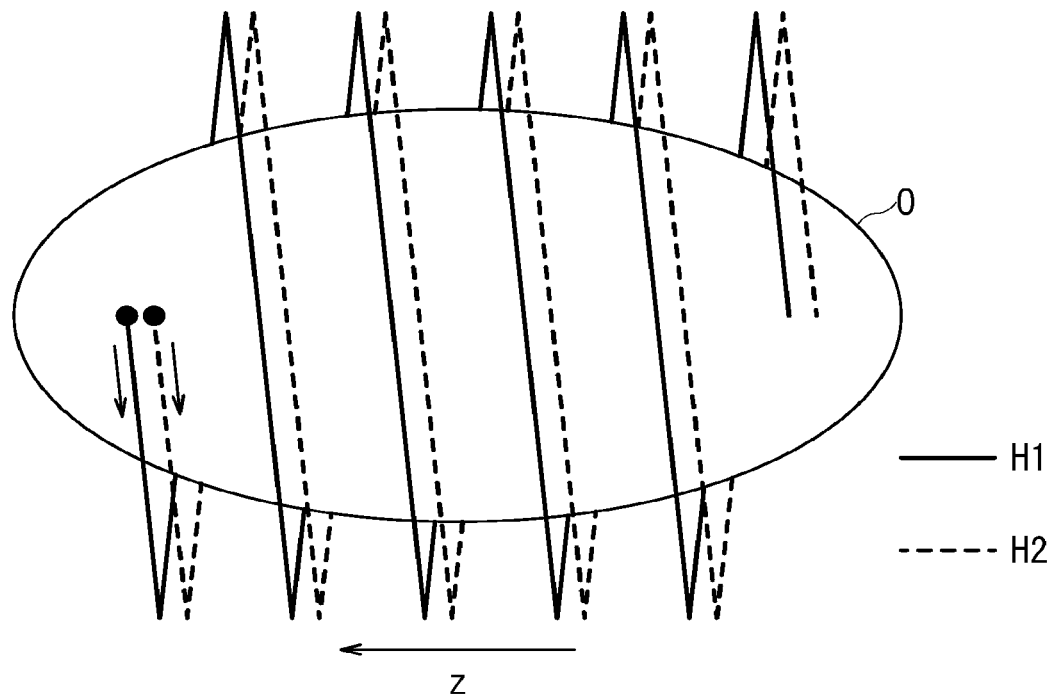
Figure 10:
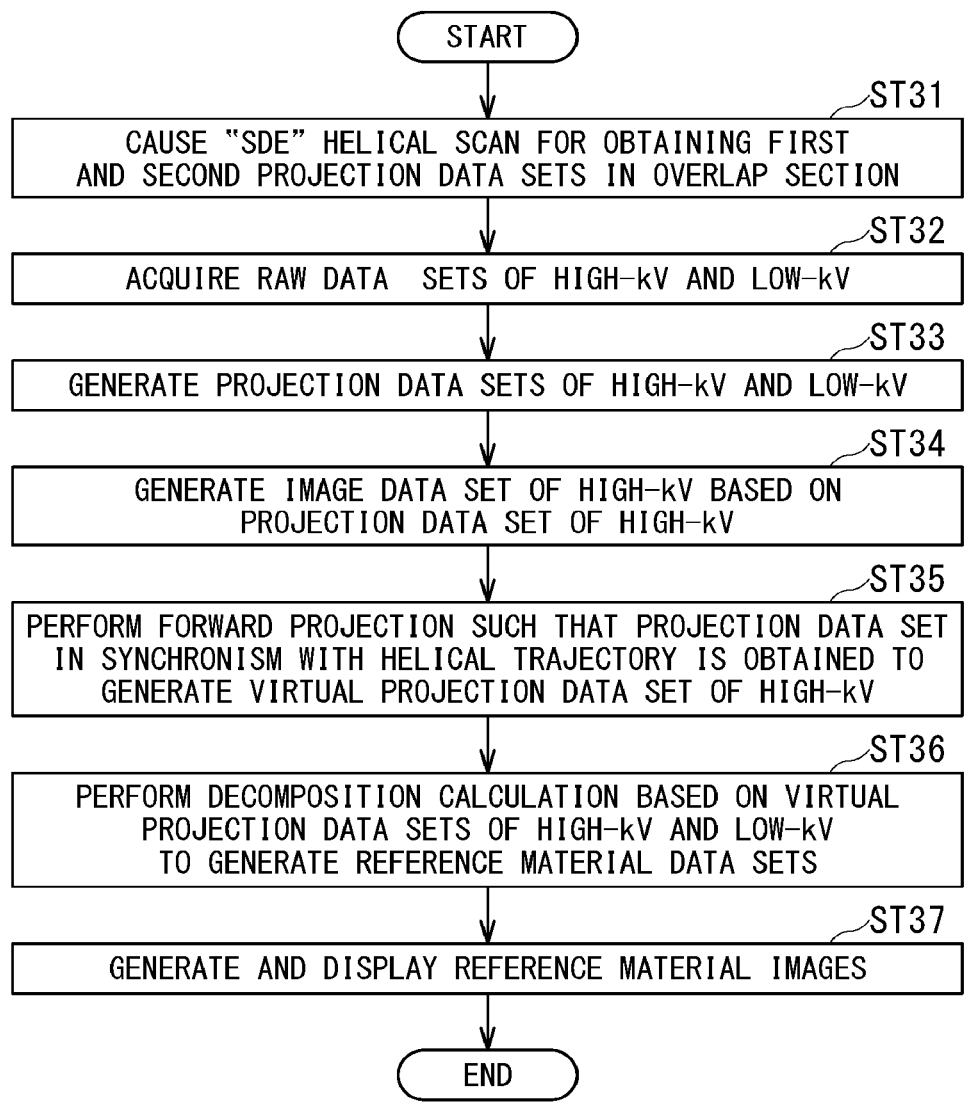
Figure 11:
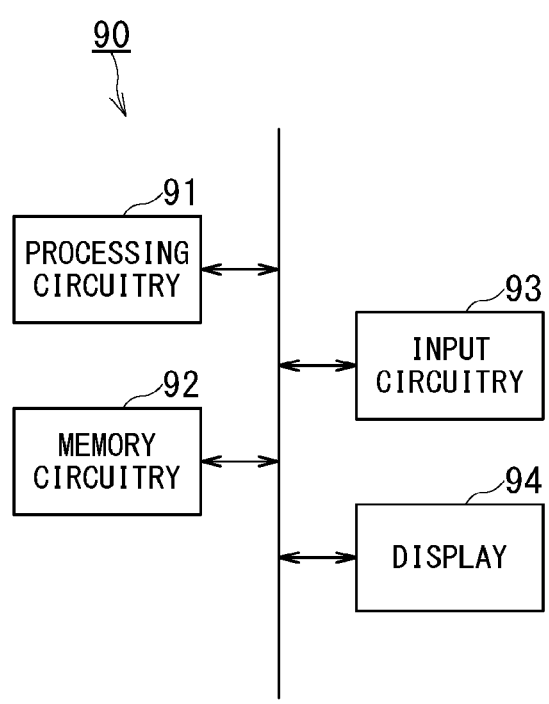
Figure 12:
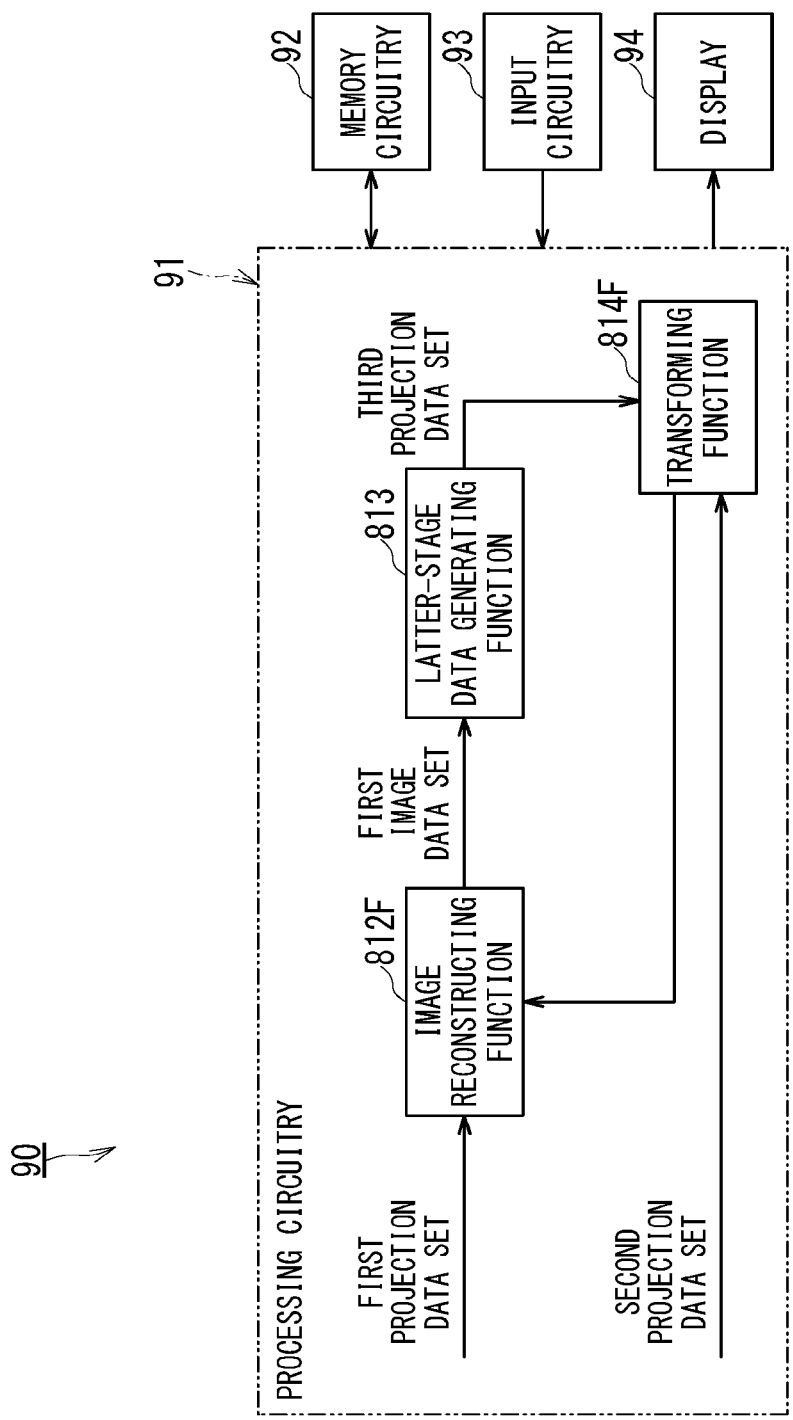
Figure 13:
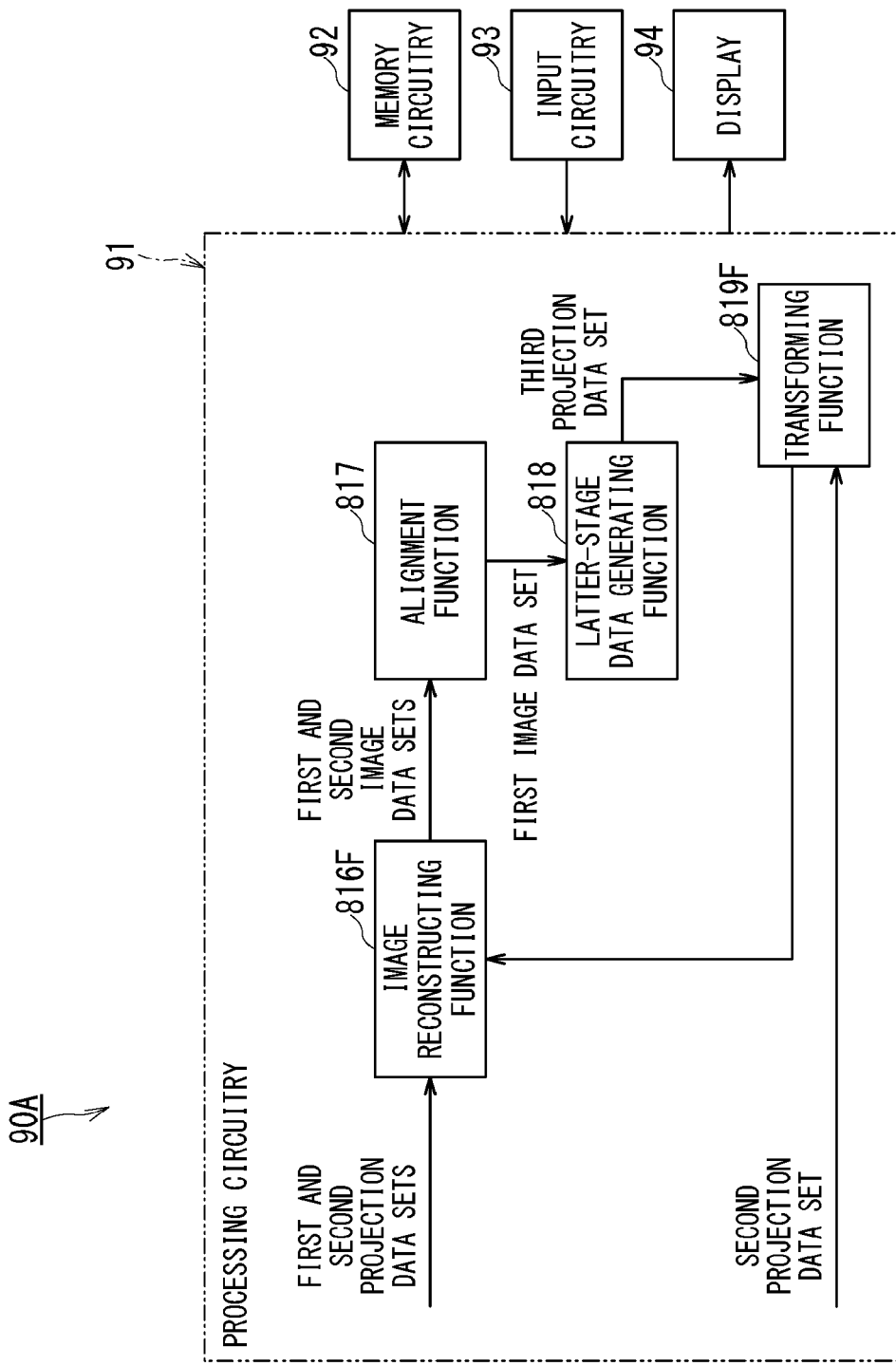
Figure 14:
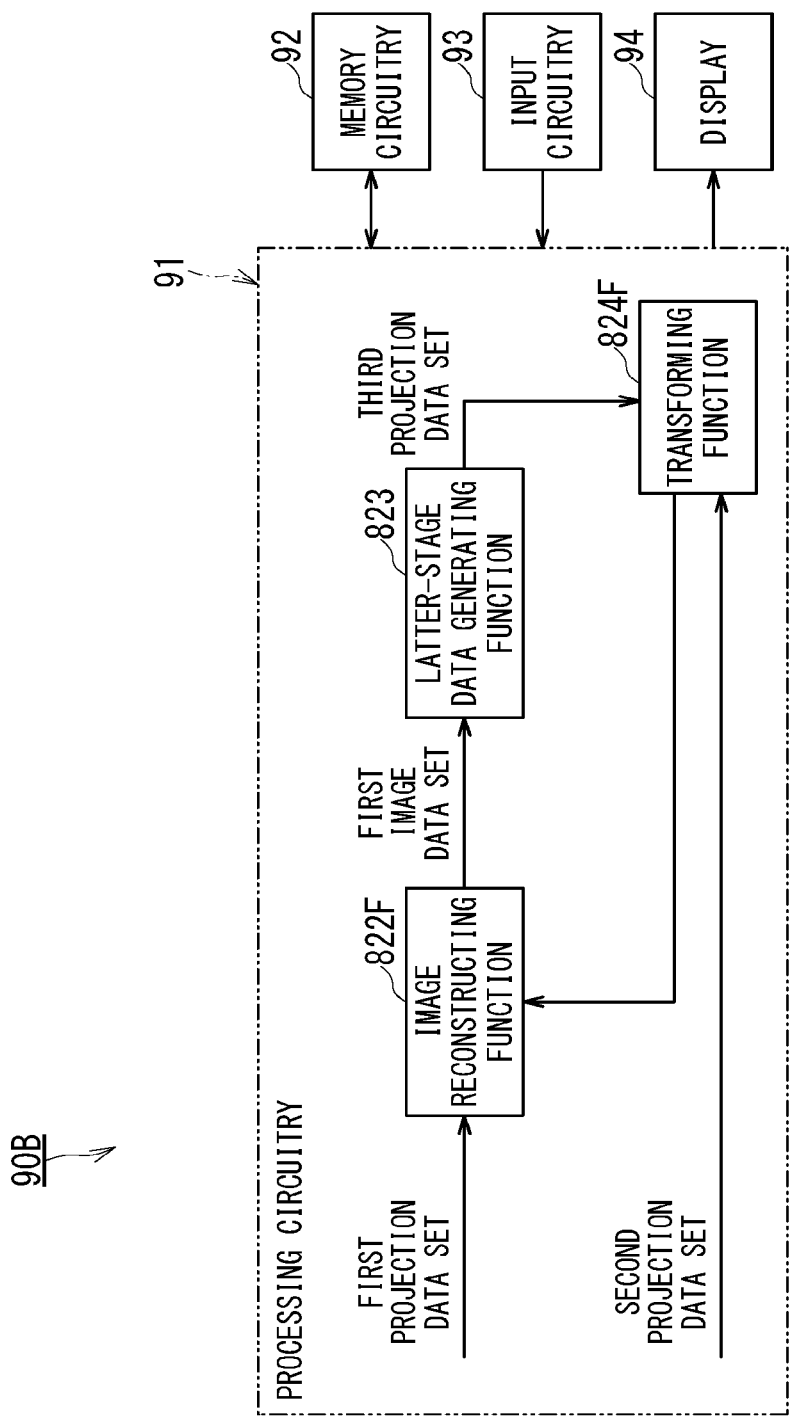

Each of FIGS. 9A and 9B is a side view schematically showing a helical trajectory of X-ray tube;

FIG. 10 is a flowchart showing an operation of the X-ray CT apparatus according to the third embodiment;

FIG. 11 is a diagram showing an exemplary configuration of a medical image processing apparatus according to a first embodiment;

FIG. 12 is a block diagram showing functions of the medical image processing apparatus according to the first embodiment;

FIG. 13 is a block diagram showing functions of a medical image processing apparatus according to a second embodiment; and FIG. 14 is a block diagram showing functions of a medical image processing apparatus according to a third embodiment.

DETAILED DESCRIPTION

An X-ray CT apparatus according to the present embodiment will be described with reference to the appended drawings.

The X-ray CT apparatus according to the present embodiment includes: an X-ray tube configured to radiate X-rays; a voltage generator configured to apply voltage to the X-ray tube; an X-ray detector configured to detect the X-rays; and processing circuitry. The processing circuitry is configured to: control the voltage generator during non-helical scan to switch tube voltage to be applied to the X-ray tube, thereby causing an imaging to be performed separately with X-rays of a first energy and X-rays of a second energy different from the first energy; generate first and second projection data sets, respectively; perform image reconstruction based on the first and second projection data sets respectively, thereby generating first and second images respectively; perform alignment processing to align the second image with the first image; generate a third projection data set based on a processing result of the alignment processing; perform transformation processing to transform the second and third projection data set into projection data sets corresponding to reference materials; and perform image reconstruction based on the projection data sets after the transformation processing, thereby generating reference material images corresponding to reference materials.

Data collection system based on an X-ray CT apparatus includes variations such as an R-R (Rotate/Rotate) system in which an X-ray tube and an X-ray detector rotate integrally around an object, and an S-R (Stationary/Rotate) system in which a large number of detection elements are arrayed in a ring form and only the X-ray tube rotates around the object. The present invention is applicable to either of the systems. Hereinafter, the X-ray CT apparatus according to the present embodiment will be explained on an exemplary case in which a third generation R-R system which is currently in dominant use is adopted.

Further, the Dual Energy Scan adopted by using the X-ray CT apparatus is carried out by any of the following four major methods. A first method is a Slow-kV switching type in which one X-ray tube is used and the tube voltage applied to the X-ray tube is switched, thereby imaging an object separately by X-rays of a first energy and X-rays of a second energy different from the first energy. Thus, in the Slow-kV switching type, after imaging for each view (rotation angle) is performed at a first tube voltage, imaging for each view is performed at a second tube voltage different from the first tube voltage. The Slow-kV switching type is also called a double-rotation type.

A second method is a Fast-kV switching type in which imaging is performed by switching the tube voltage of the X-ray tube at a high speed each time the view is changed. The Fast-kV switching type is simply called a high-speed switching type. In this case, a data collection circuitry performs data collection in synchronism with switching of the tube voltage. In the Fast-kV switching type, data sets at different tube voltages are collected substantially simultaneously unlike in the case of Dual Energy Scan of the Slow-kV switching type.

A third method is a Dual Source type in which two X-ray tubes are mounted and they are used to perform imaging for each view separately at different tube voltages. The Dual Source type is also called a double-tube type.

A fourth method is a multi-layer type which utilizes an X-ray detector having a multilayer structure. For example, when an X-ray detector having a two-layer structure including a shallow layer and a deep layer is used, X-rays of low energy are detected in the shallow layer, and X-rays of high energy are detected in the deep layer after passing through the shallow layer.

The present invention is applicable when the above described first method, that is, Dual Energy Scan of the Slow-kV switching type is carried out in the first to third embodiments. The present invention is also applicable when the above described third method, that is, Dual Energy Scan of double-tube type is carried out in the third embodiment.

Further, the present invention is also applicable when a multi-energy scan, that is, dual or more energy scan is carried out in the first to third embodiments.

X-Ray CT Apparatus According to First Embodiment

Figure 1:
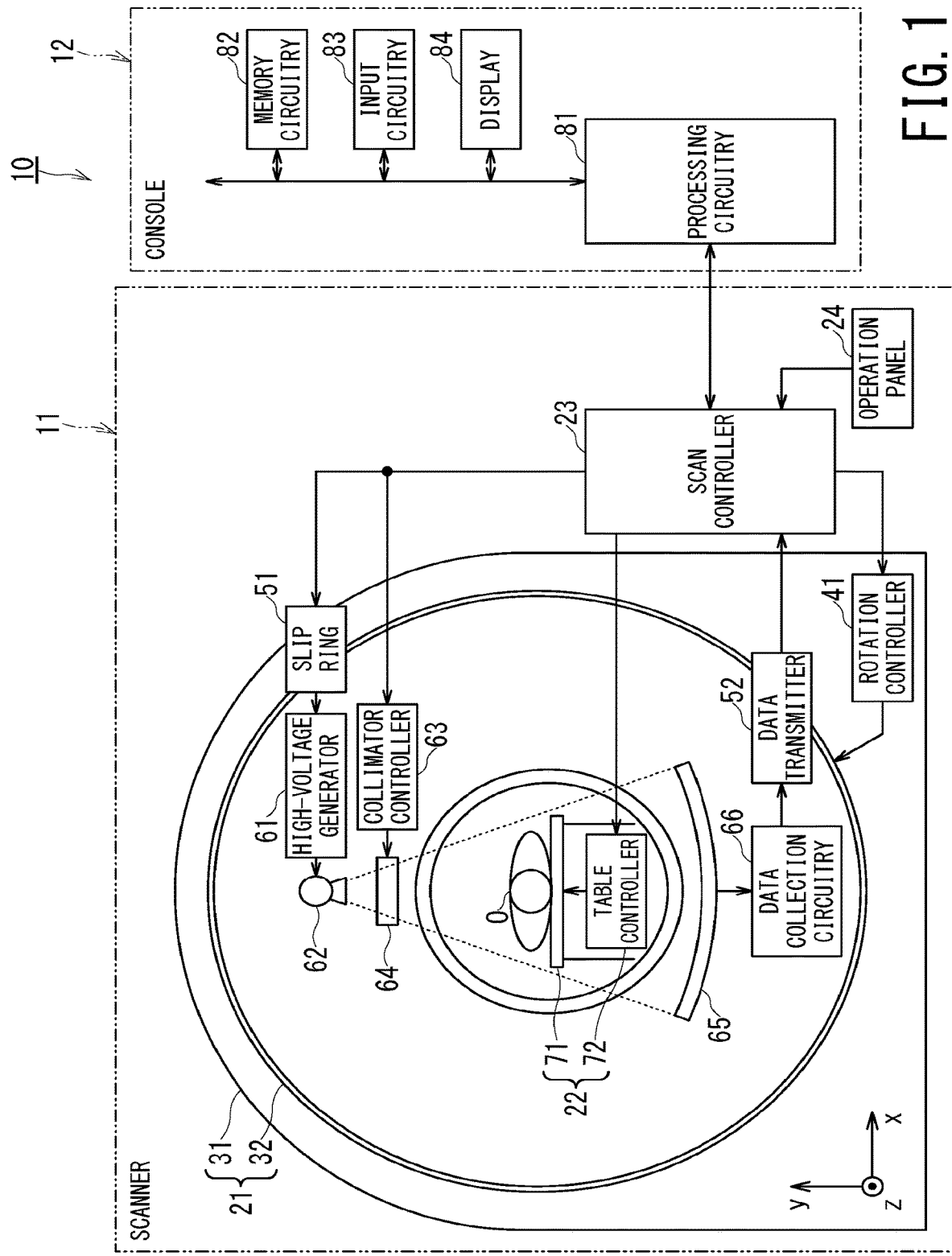
FIG. 1 is a diagram showing an exemplary configuration of an X-ray CT apparatus according to a first embodiment.

FIG. 1 is a diagram showing an exemplary configuration of an X-ray CT apparatus according to a first embodiment.

FIG. 1 shows an X-ray CT apparatus 10 which performs the Dual Energy Scan of the Slow-kV switching type, according to the first embodiment. The X-ray CT apparatus 10 includes a scanner 11 and a console 12. The scanner 11 is typically installed in an inspection room, and generates transmission data of X-rays relating to an object, for example, a patient O. On the other hand, the console 12, which is typically installed in a control room adjacent to the inspection room, generates projection data based on the transmission data, and generates and displays a reconstructed image.

The scanner 11 includes a stand apparatus 21, a bed 22, a scan controller 23, and an operation panel 24.

The stand apparatus 21, which is also called a gantry, includes a fixed stand 31 fixed to a foundation part (not shown) and a rotator 32.

The fixed stand 31 includes a rotation controller 41. The rotation controller 41 rotates the rotator 32 with respect to the fixed stand 31 according to an instruction from the scan controller 23.

The fixed stand 31 and the rotator 32 include a slip ring 51 and a data transmitter 52.

The slip ring 51 is a connector for rotating contact which allows passage of electric current while a brush such as a carbon brush and a wire brush on the side of the fixed stand 31 is pressed from sideward against a ring-shaped electric circuit (metal ring), which is disposed in a concentric manner with the rotator 32, so as to be allowed to slip to each other.

The data transmitter 52 includes a transmission circuit on the side of the rotator 32 and a reception circuit on the side of the fixed stand 31. The transmission circuit transmits raw data generated by a data collection circuitry 66 to be described below to the reception circuit in a non-contact manner. The reception circuit provides the raw data transmitted from the transmission circuit to a scan controller 23 to be described later.

The rotator 32 includes a high-voltage generator 61, an X-ray tube 62, a collimator controller 63, an X-ray optical system 64, an X-ray detector 65, and data collection circuitry 66. The rotator 32 is also called a rotatable frame. The rotator 32 holds components 61 to 66 integrally. That is, the rotator 32 can rotate integrally around the patient O with the X-ray tube 62 and the X-ray detector 65 being faced to each other. It is noted that the direction parallel with the central axis of rotation of the rotator 32 is defined as a z direction, and the plane orthogonal to the z direction is defined as an X direction and a y direction.

The high-voltage generator 61 provides power needed for executing Dual Energy Scan to the X-ray tube 62 according to a control signal by the scan controller 23 via the slip ring 51.

The X-ray tube 62 generates X-rays by causing an electron beam to collide with a target made of metal according to the tube voltage provided from the high-voltage generator 61, and radiates the X-rays toward the X-ray detector 65. A fan beam X-ray, a cone beam X-ray, and the like are formed by the X-rays radiated from the X-ray tube 62. The X-ray tube 62 is provided with power needed for radiation of X-rays through the control by the scan controller 23.

Figure 2:
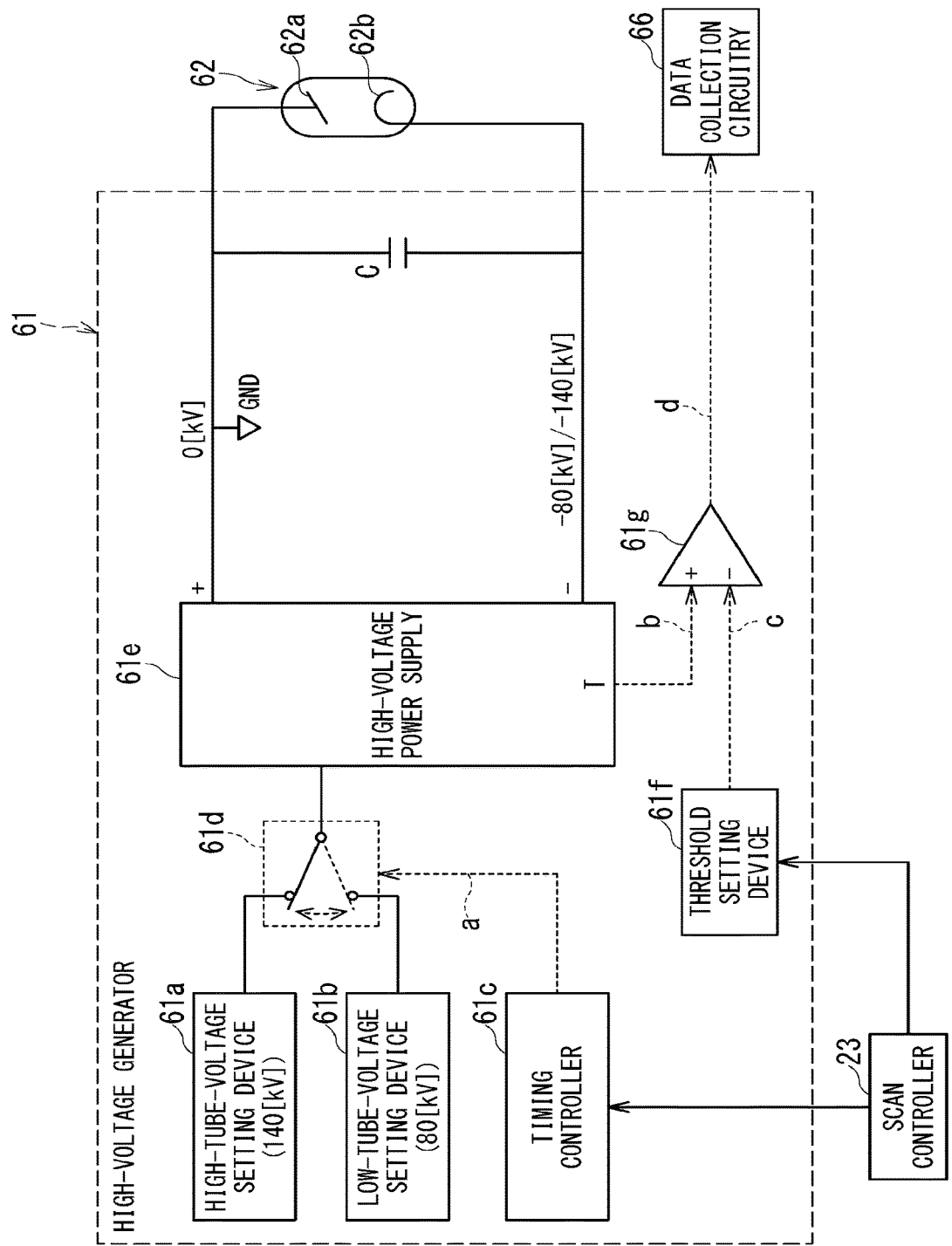
FIG. 2 is a diagram showing an exemplary configuration of a high-voltage generator and an X-ray tube, which are to be provided in the X-ray CT apparatus according to the first embodiment.

FIG. 2 is a diagram showing an exemplary configuration of a high-voltage generator 61 and an X-ray tube 62, which are to be provided in the X-ray CT apparatus 10 according to the first embodiment.

As shown in FIG. 2, the high-voltage generator 61 includes a high-tube-voltage setting device 61a, a low-tube-voltage setting device 61b, a timing controller 61c, a switch 61d, a high-voltage power supply 61e, a threshold setting device 61f, a comparator 61g, and a condenser C. Further, the X-ray tube 62 includes an anode 62a and a filament (cathode) 62b. For example, the High-kV (high tube voltage) can be set to 140 kV, and the Low-kV (low tube voltage) to 80 kV in the Dual Energy Scan.

While the high-tube-voltage setting device 61a sets the Low-kV, the low-tube-voltage setting device 61b sets the High-kV. The outputs of the tube-voltage setting devices 61a and 61b are both selectable. The output of the tube-voltage setting device 61a or 61b is connected to the high-voltage power supply 61e via the switch 61d controlled by the timing controller 61c. The switch 61d is controlled by a signal "a" outputted from the timing controller 61c. When the signal "a" indicates "H", the high-tube-voltage setting device 61a is selected, and on the other hand, when it indicates "L", the low-tube-voltage setting device 61b is selected.

The output of the plus side of the high-voltage power supply 61e is electrically connected to the anode 62a of the X-ray tube 62, and is also grounded. Moreover, the output of the minus side of the high-voltage power supply 61e is electrically connected to the filament 62b of the X-ray tube 62. The output of the high-voltage power supply 61e is switched to High-kV or Low-kV at a switching timing by the signal "a". The high-voltage power supply 61e is provided with a tube-voltage detection terminal T, and the tube-voltage detection terminal T is connected to the input of the plus side of the comparator 61g. The threshold setting device 61f is connected to the input of the minus side of the comparator 61g.

The comparator 61g receives a signal "b" inputted from the tube-voltage detection terminal T of the high-voltage power supply 61e and a signal "c" inputted from the threshold setting device 61f, and outputs to the data collection circuitry 66 a signal "d" which indicates "H" when the signal "b" is larger than the signal "c", and indicates "L" when the signal "b" is not more than the signal "c". The data collection circuitry 66 judges that when the signal "d" indicates "H", the signal "d" is a transmission data set based on High-kV, and when the signal "d" indicates "L", the signal "d" is a transmission data set based on Low-kV.

The scan controller 23 controls switching of the switch 61d via the timing controller 61c of the high-voltage generator 61 according to a tube-voltage control signal from processing circuitry 81 (shown in FIG. 1) to cause Dual Energy Scan to be performed, and selects whether to cause High-kV by the high-tube-voltage setting device 61a to be outputted from the high-voltage power supply 61e, or to cause Low-kV by the low-tube-voltage setting device 61b to be outputted from the high-voltage power supply 61e. In response to a control signal from the scan controller 23, the switch 61d provides a selected tube-voltage setting signal to the high-voltage power supply 61e.

Further, the control signal from the scan controller 23 is also sent to the data collection circuitry 66. The data collection circuitry 66 recognizes whether the data set collected by Dual Energy Scan is obtained with X-rays of High-kV, or with X-rays of Low-kV.

Referring back to FIG. 1, the collimator controller 63 adjusts the irradiation range in the slice direction of X-rays in the X-ray optical system 64 through the control by the scan controller 23.

The X-ray optical system 64 includes various instruments for controlling the radiation dose, irradiation range, shape, and radiation quality of X-ray beams. Specifically, the X-ray optical system 64 includes a wedge filter and a collimator. The wedge filter adjusts the X-ray dose of the X-rays generated at the X-ray tube 62. The collimator is a slit for reducing the irradiation range of X-rays for the X-rays of which radiation dose has been adjusted through the control by the collimator controller 63.

The X-ray detector 65 is a detector of one-dimensional array type which has multiple detection elements in the channel direction and a single detection element in the row (slice) direction. Alternatively, the X-ray detector 65 is a detector of matrix type, that is, of two-dimensional array type which has multiple detection elements in the channel direction and multiple detection elements in the slice direction. The X-ray detector 65 detects X-rays radiated from the X-ray tube 62.

The detector of two-dimensional array type is also called a multi-slice type detector. When the X-ray detector 65 is a multi-slice type detector, it is possible to perform scanning of a 3-dimensional range having a width in the row direction by one rotation (or a half rotation+α) of the rotator 32. This scanning is called a volume scan.

The data collection circuitry 66 has DASs (Data Acquisition Systems). Each DAS performs data collection in synchronism with switching of the tube voltage in Dual Energy Scan. Each DAS amplifies the signal of transmission data detected by each detection element of the X-ray detector 65, and transforms it into raw data which is a digital signal. Each DAS sends the raw data to the scan controller 23 via the data transmitter 52.

The bed 22 of the scanner 11 includes a table 71 and a table controller 72. The table 71 can place a patient O thereon.

The table controller 72 includes a mechanism to cause the table 71 to move up and down along the y direction, and to enter/retreat in the z direction through the control by the scan controller 23. The table controller 72 causes the patient O placed on the table 71 to be inserted toward an opening section including the rotational center of the rotator 32, and causes the patient O placed on the table 71 to retreat from the opening section.

The scan controller 23 includes a CPU (Central Processing Unit) not shown and a memory, etc. Upon instruction from the operation panel 24 and the console 12, the scan controller 23 controls the rotation controller 41, the high-voltage generator 61, and the collimator controller 63 of the stand apparatus 21, and the table controller 72 of the bed 22, thereby causing Dual Energy Scan and the like to be performed.

The scan controller 23 can also perform Dual Energy Scan of the Slow-kV switching type in combination with a helical scan. The helical scan is a scan for performing radiation and detection of X-rays with the rotator 32 being rotated while the table 71 (or the stand apparatus 21) is being moved in sliding in the z direction. Hereinafter, a scan which combines Dual Energy Scan of the Slow-kV switching type with the helical scan is referred to as "SDE helical scan". The SDE helical scan may be adopted in the first and third embodiments.

Further, the scan controller 23 can also perform Dual Energy Scan of the Slow-kV switching type in combination with a conventional scan which is a non-helical scan. The conventional scan performs radiation and detection of X-rays with the rotator 32 being rotated while the table 71 (or the stand apparatus 21) is stopped in the z direction. Hereinafter, a scan which combines Dual Energy Scan of the Slow-kV switching type with a conventional scan is referred to as "SDE conventional scan". The SDE conventional scan may be adopted in the second embodiment.

Further, the scan controller 23 can also perform Dual Energy Scan of the double-tube type in combination with a helical scan. Hereinafter, a scan which combines the Dual Energy Scan of the double-tube type with the helical scan is referred to as "two-tube DE helical scan". The two-tube DE helical scan may be adopted in the third embodiment.

The operation panel 24, which is provided on both sides or in the front and rear of the opening section of the stand apparatus 21, accepts operations which the operator performs while confirming the status of the patient O. Specifically, it accepts an instruction of turning on or off a projector (not shown) for emitting light with which the operator visually confirms a detection range, and instructions of moving, stopping, and automatically feeding the table 71.

The console 12 of the X-ray CT apparatus 10, which is composed based on a computer, can mutually communicate with external apparatuses via a network such as LAN (Local Area Network). The console 12 is made up of basic hardware elements such as processing circuitry 81, memory circuitry 82, input circuitry 83, and a display 84. The processing circuitry 81 is interconnected with each hardware component, which constitutes the console 12, via a bus as a common signal transmission line. It is noted that the console 12 may include a storage medium drive.

The processing circuitry 81 means any one of dedicated or general central processing unit (CPU) and a micro processor unit (MPU), an application specific integrated circuit (ASIC), and a programmable logic device. The programmable logic device may be, for example, any one of a simple programmable logic device (SPLD), a complex programmable logic device (CPLD), a field programmable gate array (FPGA) and the like. The processing circuitry 81 reads programs stored in the memory circuitry 82 or directly implemented in the processing circuitry 81 and executes these programs to achieve the following functions.

The processing circuitry 81 may be a single processing circuit or a combination of multiple processing circuits. In the latter case, the memory circuitry 82 includes multiple memory circuits each storing an element of a program, each of the multiple memory circuits is provided for each of the multiple circuits. Alternatively, the memory circuitry 82 includes a single memory circuit storing the program, the single memory circuit is provided for the multiple processing circuits.

The memory circuitry 82 is made up of semiconductor memory devices such as a RAM (Random Access Memory) and a flash memory, hard discs, optical discs, and the like. The memory circuitry 82 may be made up of portable media such as a USB (Universal Serial Bus) memory and a DVD (Digital Video Disk). The memory circuitry 82 stores various processing programs (including application programs, as well as an OS (Operating System)) used in the processing circuitry 81, data necessary for executing the programs, and image data. Moreover, the OS may include a GUI (Graphic User Interface) which frequently uses graphics for displaying information for the operator on the display 84, and allows basic operations to be performed by use of the input circuitry 83.

The input circuitry 83 is a circuit for receiving input of a signal from an input device such as a pointing device which can be operated by the operator. Here, it is assumed that the input device itself is included in the input circuitry 83. When the input device is operated by the operator, the input circuitry 83 generates a signal corresponding to the operation and outputs it to the processing circuitry 81. It is noted that the console 12 may include a touch panel in which an input device is integrated with the display 84.

The display 84 is a display device such as a liquid crystal display panel, a plasma display panel, and an organic EL (Electro Luminescence) panel. The display 84 displays image data according to control by the processing circuitry 81.

The console 12 performs logarithmic transformation processing and correction processing such as sensitivity correction processing, that is, preprocessing on the raw data inputted from the scanner 11 to generate projection data, and causes it to be stored in the memory circuitry 82. The console 12 performs processing to remove scattered radiation on the preprocessed projection data. The console 12, which is configured to perform removing processing of scattered radiation based on the value of the projection data within the range of X-ray exposure, performs correction of scattered radiation by subtracting scattered radiation, which is estimated from the magnitude of the value of projection data to be subjected to the correction of scattered radiation or adjacent projection data thereof, from the projection data to be processed. Hereinafter, data not subjected to correction of scattered radiation, and data subjected to correction of scattered radiation are referred to as projection data.

The console 12 generates image data based on the projection data and causes it to be stored in the memory circuitry 82 and to be displayed on the display 84.

Next, functions of the X-ray CT apparatus 10 according to the first embodiment will be described.

Figure 3:
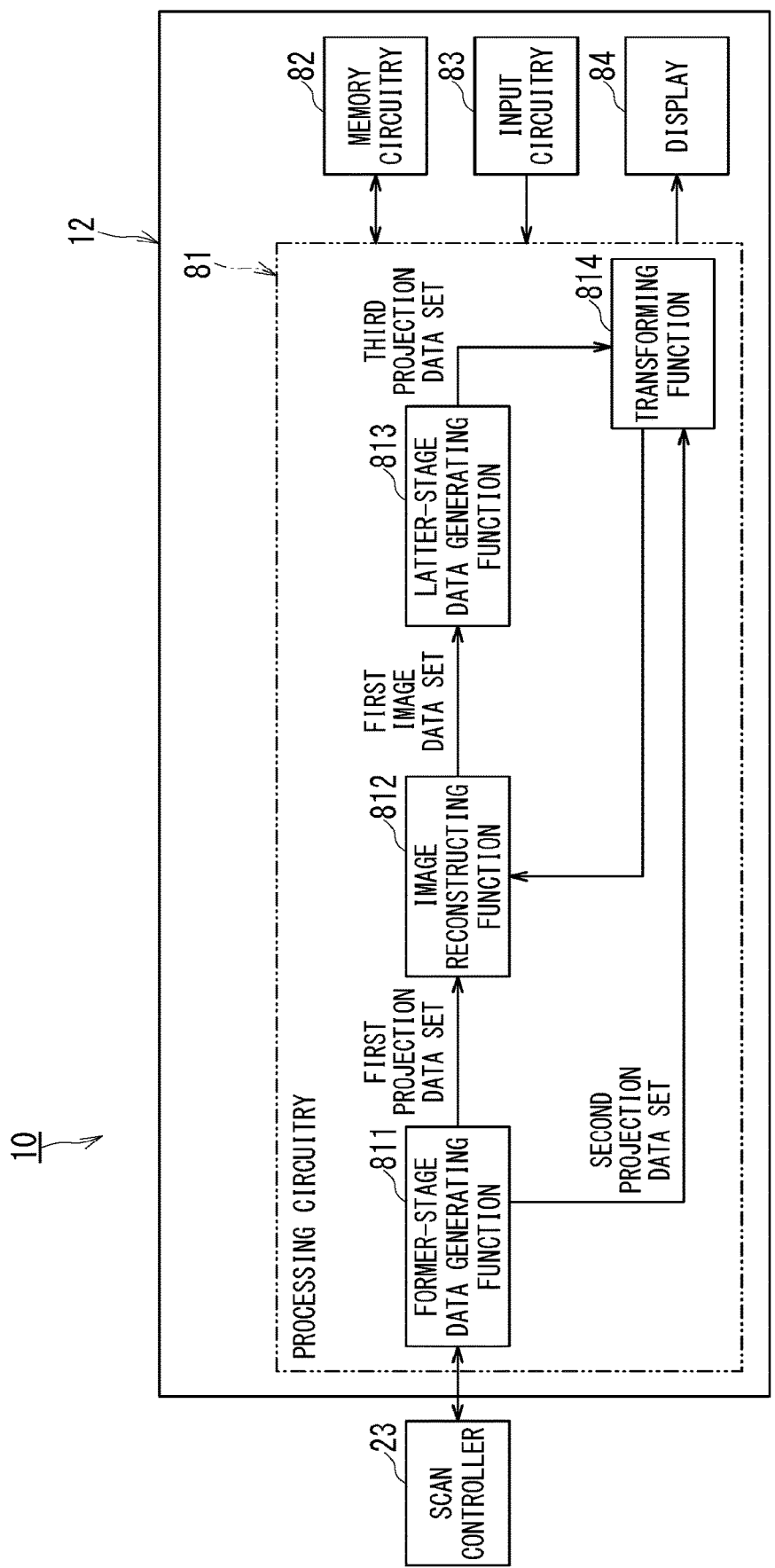
FIG. 3 is a block diagram showing functions of the X-ray CT apparatus according to the first embodiment.

FIG. 3 is a block diagram showing functions of the X-ray CT apparatus 10 according to the first embodiment.

As a result of the processing circuitry 81 of the console 12 executing a program, the X-ray CT apparatus 10 functions as a former-stage data generating function 811, an image reconstructing function 812, a latter-stage data generating function 813, and a transforming function 814. It is noted that all or some of the functions 811 to 814 may be provided as hardware in the console 12. Further, all or some of the functions 811 to 814 may be provided not only in the console 12, but also in the scan controller 23.

The functions 811 to 814 perform dual energy reconstruction based on projection data sets (or raw data sets), rather than dual energy reconstruction based on image data sets, based on two kinds of first and second projection data sets, which are obtained respectively at two kinds of tube voltages by SDE helical scan. Here, the dual energy reconstruction based on the image data sets performs reconstruction processing based on two kinds of first and second projection data sets, respectively, to generate two kinds of first and second image data sets, and performs decomposition calculation on the first and second image data sets to generate reference material images. On the other hand, the Dual Energy reconstruction performs, in a non-helical scan, decomposition calculation respectively on a pair (Low-kV and High-kV) of actual measured projection data sets at same slice center position, and thereafter generates reference material images.

The former-stage data generating function 811 controls the high-voltage generator 61 (shown in FIG. 1) via the scan controller 23 to switch the tube voltage to be applied to the X-ray tube 62 (shown in FIG. 1), thereby causing an imaging of a patient O to be performed separately by X-rays of a first energy and X-rays of a second energy different from the first energy during SDE helical scan, and generating first and second projection data sets for different imaging sections, respectively. The different imaging sections are shown, for example in FIG. 5A. Then, the former-stage data generating function 811 causes the projection data sets to be stored in the memory circuitry 82. The former-stage data generating function 811 can perform volume scan when the X-ray detector 65 (shown in FIG. 1) is a multi-slice type detector.

The image reconstructing function 812 performs image reconstruction based on the first projection data set generated by the former-stage data generating function 811, thereby generating a first image data set. As the image reconstruction method, analytical methods typified by a convolution back projection (CBP) method and filtered back projection (FBP) method, and algebraic methods are known and used. The algebraic method is called an iterative reconstruction (IR) method since it generally uses an iterative method to obtain a reconstruction image.

The latter-stage data generating function 813 generates a third projection data set based on the first image data set generated by the image reconstructing function 812. The latter-stage data generating function 813 performs processing such as forward projection and processing using the Projection Slice Theorem on the first image data set to generate the third projection data set. The forward projection means a processing to obtain projection data set by performing line integration of physical quantities on each straight line toward the X-ray detector based on physical quantity distribution on an image. The processing using the Projection Slice Theorem means a processing to obtain projection data set by performing one dimensional Fourier inverse transformation on one dimensional data which passes through the origin in two dimensional Fourier transformation of an image. That is, the Projection Slice Theorem takes advantage of a principle that data which is obtained after subjecting projection data to one dimensional Fourier transformation corresponds to one dimensional data of the same angle which passes the origin in the two dimensional Fourier transformation of an image.

The latter-stage data generating function 813 may perform processing such as forward projection on a portion of the first image data set, the portion corresponding to a section (a specific imaging section RH shown in FIG. 5D) being same as the imaging section corresponding to the second projection data set.

The transforming function 814 transforms the second projection data set generated by the former-stage data generating function 811 and the third projection data set generated by the latter-stage data generating function 813 into projection data sets corresponding to reference materials. The transforming function 814 may use a portion of the second projection data set, the portion corresponding to the section (the specific imaging section RH shown in FIG. 5D) being same as the imaging section corresponding to the second projection data set, and a portion of the third projection data set, the portion corresponding to a section (a specific imaging section RL shown in FIG. 5E) being same as the imaging section corresponding to the second projection data set.

Here, the image reconstructing function 812 performs image reconstruction based on the projection data set after transformation by the transforming function 814, thereby generating reference-material image data set corresponding to reference materials. The reference-material image data is also called reference material enhanced image data.

The image reconstructing function 812 uses the projection data set after transformation by the transforming function 814 to separate (discriminate) predetermined reference materials which exist in a target range of an imaging. The reference material includes, for example, a contrast medium, $CaCo_3$, uric acid, and fat. The image reconstructing function 812 reconstructs the reference-material image data sets for each selected reference material. For example, the image reconstructing function 812 generates a reference-material image data set relating to a first reference material based on the projection data set corresponding to the first reference material, and generates a reference-material image data set relating to a second reference material based on the projection data set corresponding to the second reference material.

Details of the functions 811 to 814 will be described below.

Figure 4:
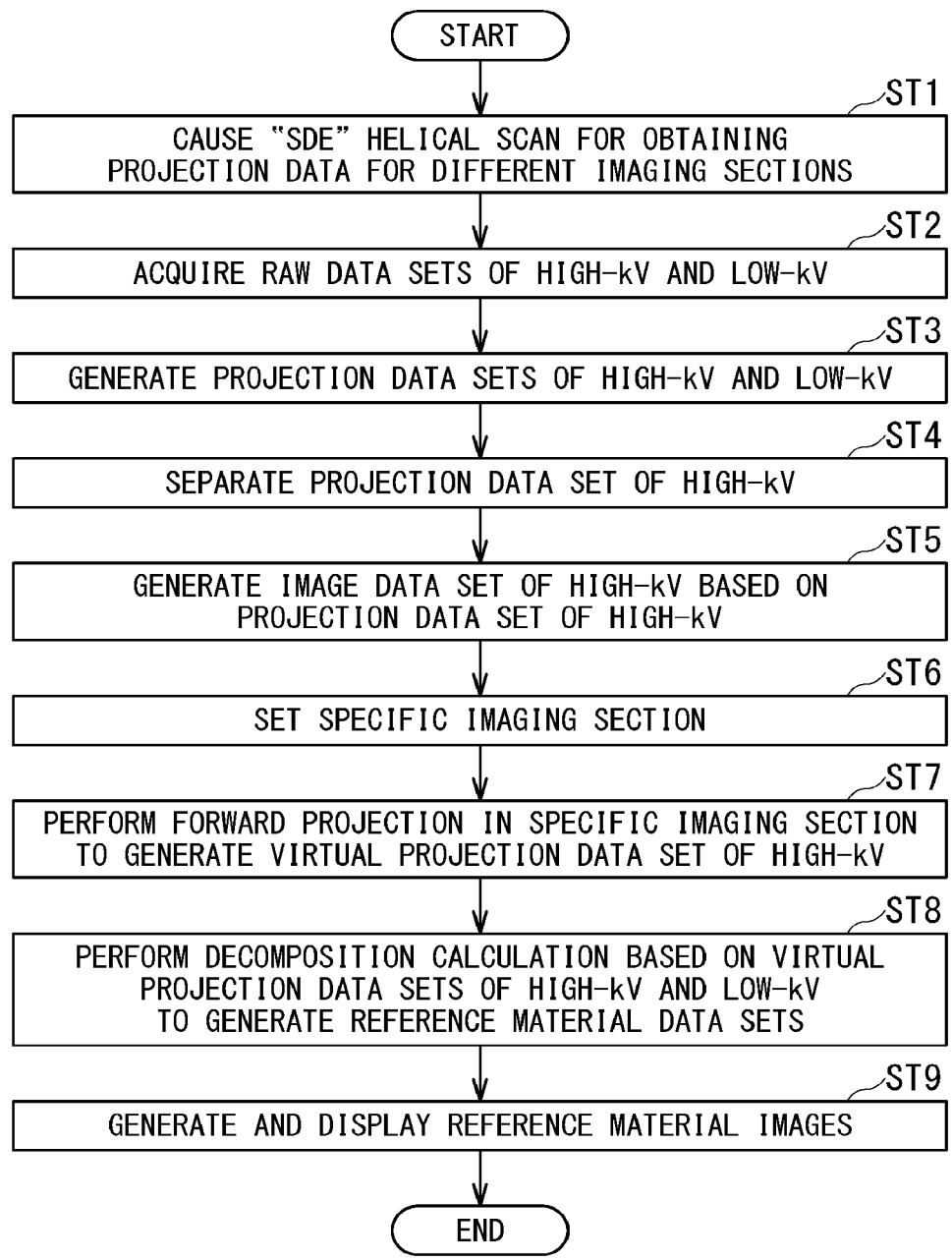
FIG. 4 is a flowchart showing an operation of the X-ray CT apparatus according to the first embodiment.

FIG. 4 is a flowchart showing an operation of the X-ray CT apparatus 10 according to the first embodiment. FIGS. 5A to 5F are diagrams showing a concept of data structure.

Here, description will be made assuming that the first projection data set and the first image data set obtained at a first tube voltage relating to the SDE helical scan are a projection data set of High-kV and an image data set of High-kV, and that the second projection data set and the second image data set obtained at a second tube voltage are a projection data set of Low-kV and an image data set of Low-kV.

The former-stage data generating function 811 controls the scan controller 23 with a patient O being placed on the table 71, to cause the SDE helical scan for obtaining projection data sets of high-kV and Low-kV for different imaging sections to be executed (step ST1).

The former-stage data generating function 811 acquires a raw data set of High-kV and a raw data set of Low-kV from the scan controller 23 by the SDE helical scan at step ST1 (step ST2). The former-stage data generating function 811 generates a projection data set of High-kV from the raw data set of High-kV acquired at step ST2, and generates a projection data set of Low-kV from the raw data set of Low-kV (step ST3).

Figure 5A:
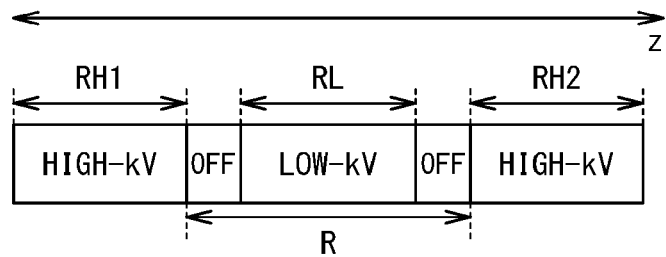
FIGS. 5A to 5F are diagrams showing a concept of data structure.

Here, it is assumed that during the SDE helical scan, (1) an imaging over multiple views with High-kV, (2) X-ray radiation OFF for tube modification, (3) an imaging over multiple views with Low-kV, and (4) X-ray radiation OFF for tube modification, and an imaging over multiple views with High-kV are carried out in order, while the table 71 is being moved in the z direction. In that case, as shown in FIG. 5A, (1) an imaging section RH1 in which a first imaging with X-rays of High-kV is performed, (2) section of X-ray radiation OFF, (3) an imaging section RL in which an imaging with X-rays of Low-kV is performed, (4) section of X-ray radiation OFF, and (5) an imaging section RH2 in which a second imaging with X-rays of High-kV is performed, occur in order in the z direction. For example, when SDE helical scan is performed on the abdomen of the patient O, the above described (1) to (5) will occur during about 30 seconds.

Each of the imaging sections RH1 and RH2 shows a section including a position of the X-ray tube 62 in the z direction (hereinafter, referred to as a "z-tube position") at which an imaging with an X-rays of High-kV is performed. The imaging section RL shows a section including a z-tube position at which an imaging with an X-rays of Low-kV is performed.

In the sections of the above described (1) to (5), in the SDE helical scan, there is no pair (Low-kV and High-kV) of actual measured projection data sets at same slice center position. A section R shown in FIG. 5A is an example of section in which no such pair exists.

That is, in the imaging sections RH1 and RH2, there exists projection data set (or raw data) of High-kV relating to slice center position of the X-ray detector 65 (shown in FIG. 1). On the other hand, in the imaging section RL, there exists no projection data set of High-kV relating to slice center position, and there exists projection data set relating to a position other than the slice center position, due to a cone angle of an X-ray beam (X-raybeam spread in z-direction). In the imaging section RL, a projection data set of Low-kV relating to a slice center position exists. On the other hand, in the imaging sections RH1 and RH2, there exists no projection data relating to slice center position, and there exists projection data set relating to a position other than the slice center position, due to a cone angle of X-rays.

According to at least one of control to increase the rotational speed of the rotator 32 to be not less than a threshold value during SDE helical scan, and control to decrease the moving speed of the table 71 in the z direction (feed speed of the patient O) during SDE helical scan, there extensively exists projection data set of High-kV relating to a position other than the slice center position in a section R. In the first embodiment, a virtual projection data set of High-kV is generated from a reconstruction image based on the projection data set of High-kV. The virtual projection data set of High-kV corresponds to the projection data set of Low-kV relating to the slice center position in the imaging section RL.

Figure 5B:
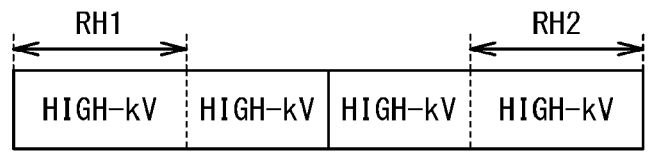

Referring back to FIGS. 3 and 4, the image reconstructing function 812 separates projection data set of High-kV generated at step ST3 (step ST4). The concept of step ST4 is shown in FIG. 5B. As shown in FIG. 5B, the projection data set of High-kV to be separated is the projection data set relating to the slice center positions in the imaging sections RH1 and RH2, as well as a projection data set relating to a position other than the slice center position in the section R.

Figure 5C:
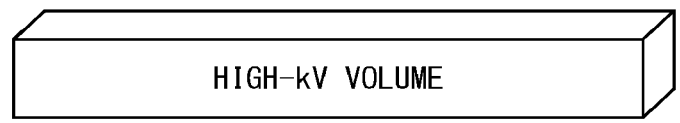

Referring back to FIGS. 3 and 4, the image reconstructing function 812 performs image reconstruction based on the projection data set of High-kV separated at step ST4, thereby generating an image data set of High-kV (step ST5). In step ST5, the image data set of High-kV is generated as volume data set as shown in FIG. 5C.

Figure 5D:
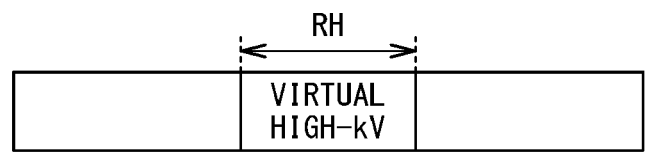
Figure 5E:
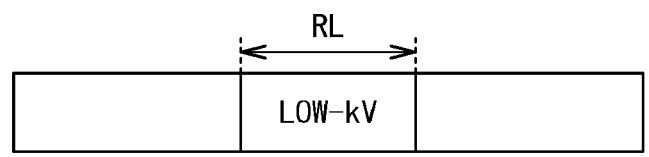

Referring back to FIGS. 3 and 4, the latter-stage data generating function 813 sets the imaging section of High-kV corresponding to the imaging section RL of Low-kV (shown in FIG. 5A) as a specific imaging section RH (shown in FIG. 5D) (step ST6). The latter-stage data generating function 813 performs processing such as forward projection in the specific imaging section RH set at step ST6 based on the image data set of High-kV generated at step ST5, thereby generating a virtual projection data set of High-kV relating to the specific imaging section RH (step ST7). The concept of step ST7 is shown in FIG. 5D.

Figure 5F:
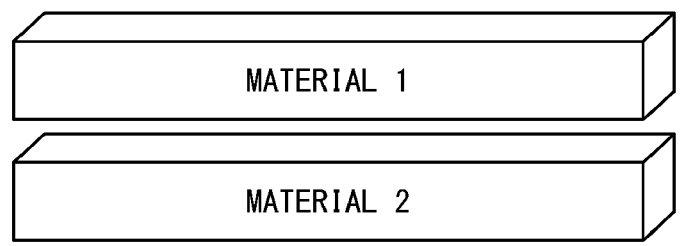

Referring back to FIGS. 3 and 4, the transforming function 814 performs decomposition calculation based on the virtual projection data set of High-kV relating to the specific imaging section RH generated at step ST7 (shown in FIG. 5D), and the projection data set of Low-kV relating to the imaging section RL (shown in FIG. 5E), to calculate reference material data sets which indicate a path length of the reference material (step ST8). The concept of two kinds of reference-material image data sets (Materials 1 and 2) generated at step ST8 is shown in FIG. 5F.

Referring back to FIGS. 3 and 4, the image reconstructing function 812 generates reference material images from the respective reference material data sets generated at step ST8, and displays them on the display 84 (step ST9).

At step ST4 shown in FIG. 4, while the image reconstructing function 812 generates two kinds of reference material images at step ST9 by separating the projection data set of High-kV, it can also generate two kinds of reference material images by separating the projection data set of Low-kV as well. When two kinds of separation are performed, the image reconstructing function 812 will generate two sets of reference material images of different phases. The image reconstructing function 812 can also mitigate discontinuity of CT value caused by the z-tube position by adding and averaging corresponding kinds of images of the two sets of reference material images, and thereby generating two kinds of reference material images.

Moreover, in steps ST1 to ST9, processing is carried out assuming that there are no effects of peristalsis of intestinal tract, respiratory movement, and body movement of a patient O during SDE helical scan. The image reconstructing function 812 generates an image data set of Low-kV by performing image reconstruction based on the projection data of Low-kV, and the latter-stage data generating function 813 may use, instead of the image data set of High-kV itself generated at step ST5, an image data set of High-kV after alignment with reference to the image data set of Low-kV, at step ST7. In that case, the latter-stage data generating function 813 can also mitigate the effects of peristalsis of intestinal tract, respiratory movement, and body movement of a patient O, by performing processing such as forward projection by using the image data set of High-kV after alignment.

The X-ray CT apparatus 10 according to the first embodiment makes it possible to realize high-precision dual energy reconstruction based on projection data sets obtained by SDE helical scan, which cannot be realized by conventional art. That is, the X-ray CT apparatus 10 according to the first embodiment generates a virtual projection data set for a specific imaging section where a projection data set corresponding to an image data set is not existent, thereby enabling high-precision dual energy reconstruction based on the projection data sets obtained by SDE helical scan.

X-Ray CT Apparatus According to Second Embodiment

Since the configuration of an X-ray CT apparatus 10A according to a second embodiment is similar to that of the X-ray CT apparatus 10 shown in FIG. 1, description thereof will be omitted.

Next, the functions of the X-ray CT apparatus 10A according to the second embodiment will be described.

Figure 6:
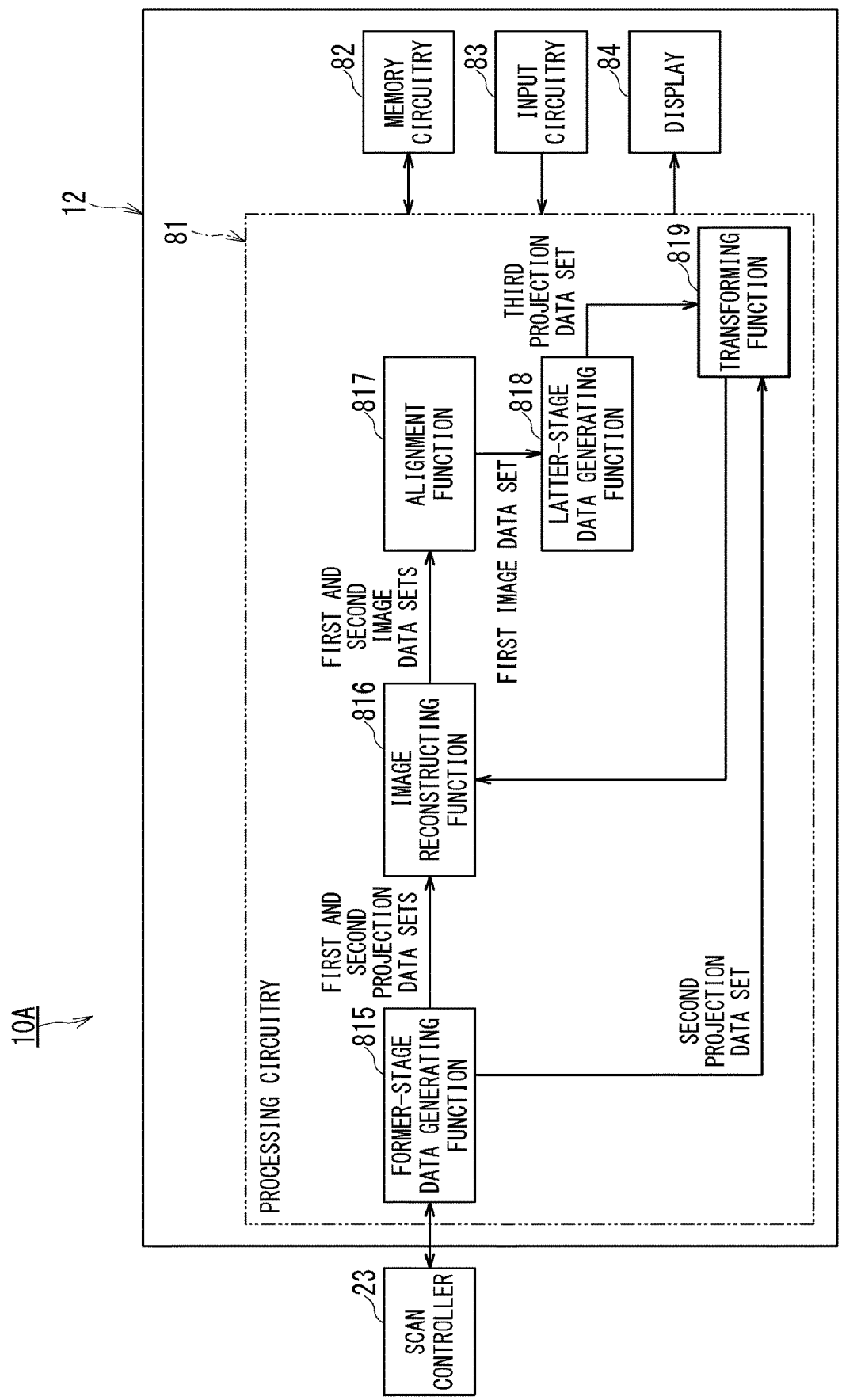
FIG. 6 is a block diagram showing functions of an X-ray CT apparatus according to a second embodiment.

FIG. 6 is a block diagram showing functions of the X-ray CT apparatus 10A according to the second embodiment.

As a result of a processing circuitry 81 of a console 12 executing a program, the X-ray CT apparatus 10A functions as a former-stage data generating function 815, an image reconstructing function 816, an alignment function 817, a latter-stage data generating function 818, and a transforming function 819. It is noted that all or some of the functions 815 to 819 may be provided as hardware in the console 12. Further, all or some of the functions 815 to 819 may be provided not only in the console 12, but also in the scan controller 23.

The functions 815 to 819 perform dual energy reconstruction based on projection data sets, rather than dual energy reconstruction based on image data set, based on two kinds of first and second projection data sets, which are obtained respectively at two kinds of tube voltages by SDE conventional scan.

The former-stage data generating function 815 controls the high-voltage generator 61 (shown in FIG. 1) via the scan controller 23 to switch the tube voltage to be applied to the X-ray tube 62 (shown in FIG. 1), and thereby causes an imaging of a patient O to be performed separately with X-rays of a first energy and X-rays of a second energy different from the first energy, thereby generating first and second projection data sets, respectively. Specifically, the former-stage data generating function 815 causes an imaging to be performed by SDE conventional scan. The former-stage data generating function 815 can perform volume scan when the X-ray detector 65 (shown in FIG. 1) is a multi-slice type detector.

The image reconstructing function 816 performs image reconstruction respectively based on the first and second projection data sets generated by the former-stage data generating function 815, and generates first and second image data set respectively.

The alignment function 817 performs alignment processing of the first image data set generated by the image reconstructing function 816, and thereby causes the first image data set to be aligned with the second image data set generated by the image reconstructing function 816.

The latter-stage data generating function 818 performs processing such as forward projection on the first image after alignment by the alignment function 817 to generate a third projection data set.

The transforming function 819 transforms the second projection data set generated by the former-stage data generating function 815 and the third projection data set generated by the latter-stage data generating function 818 into projection data sets corresponding to reference materials.

Here, the image reconstructing function 816 performs image reconstruction based on the projection data sets after transformation by the transforming function 819, thereby generating reference material images corresponding to reference materials.

Details on the functions 815 to 819 will be described below.

Figure 7:
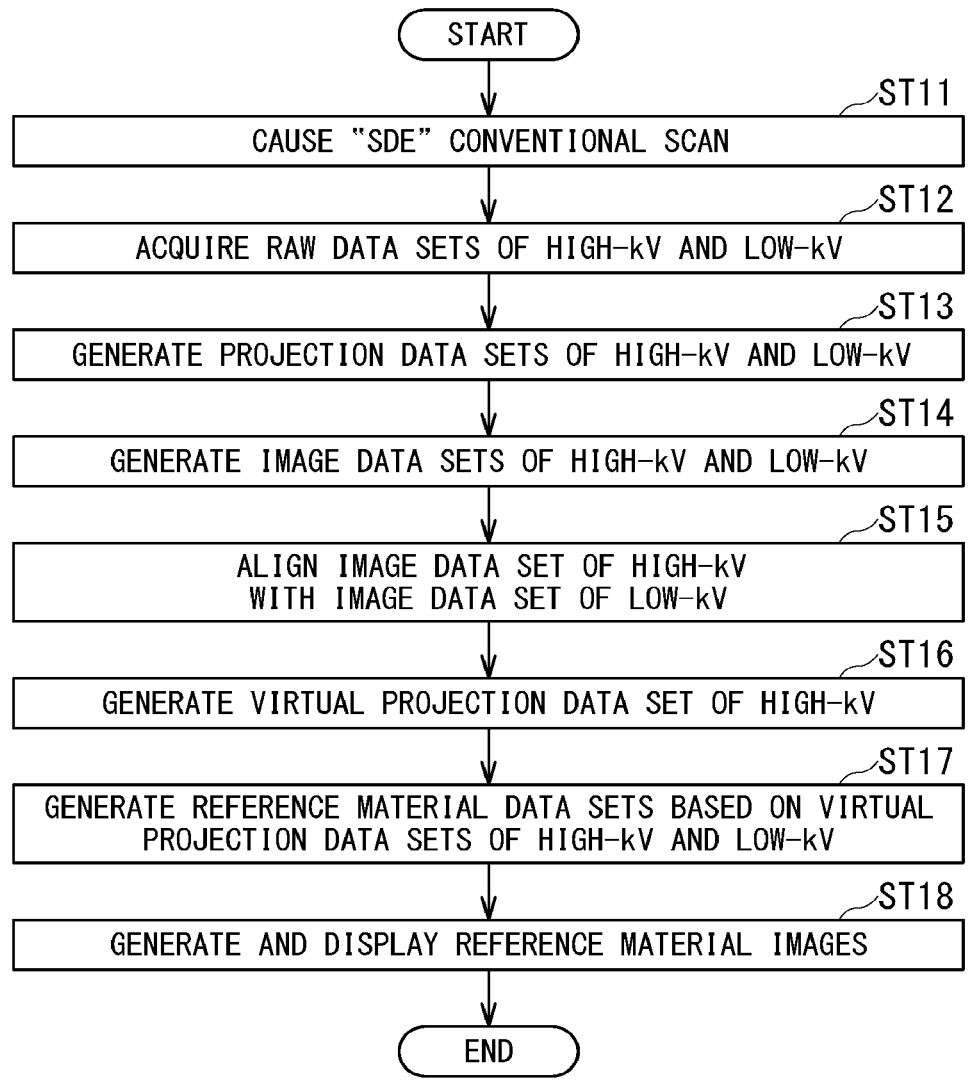
FIG. 7 is a flowchart showing an operation of the X-ray CT apparatus according to the second embodiment.

FIG. 7 is a flowchart showing an operation of the X-ray CT apparatus 10A according to the second embodiment.

Here, description will be made assuming that the first projection data set and the first image data set obtained by the first tube voltage relating to the SDE conventional scan are a projection data set of High-kV and an image data set of High-kV, and that the second projection data set and the second image data set obtained by the second tube voltage are a projection data set of Low-kV and an image data set of Low-kV.

The former-stage data generating function 815 controls the scan controller 23 with a patient O placed on the table 71, to cause the SDE conventional scan to be executed (step ST11).

The former-stage data generating function 815 acquires a raw data set of High-kV and a raw data set of Low-kV from the scan controller 23 by the SDE conventional scan at step ST11 (step ST12). The former-stage data generating function 815 generates a projection data set of High-kV from the raw data set of High-kV acquired at step ST12, and generates a projection data set of Low-kV from the raw data set of Low-kV (step ST13).

The image reconstructing function 816 performs image reconstruction respectively based on the projection data set of High-kV and the projection data set of Low-kV, which are generated at step ST13, thereby generating an image data set of High-kV and an image data set of Low-kV, respectively (step ST14).

The alignment function 817 performs aligning processing of the image data set of High-kV generated at step ST14, thereby aligning the image data set of High-kV with the image data set of Low-kV generated at step ST14 (step ST15). The alignment function 817 performs aligning processing of the image data set of High-kV by using conventional processing such as liner transformation and non-linear transformation.

The latter-stage data generating function 818 performs processing such as forward projection based on the image data set of High-kV after alignment at step ST15, thereby generating a virtual projection data set of High-kV (step ST16).

The transforming function 819 performs decomposition calculation based on the projection data set of Low-kV generated at step ST13 and the virtual projection data set of High-kV generated at step ST16, thereby calculating reference material data sets which are the path length of the reference material (step ST17). The image reconstructing function 816 generates reference material images from the respective reference material data set generated at step ST17, and displays them on the display 84 (step ST18).

As a result of the alignment function 817 aligning image of High-kV with image of Low-kV at step ST15 shown in FIG. 7, and the latter-stage data generating function 818 performing processing such as forward projection based on the image data set of High-kV after alignment at step ST16, the image reconstructing function 816 generates two kinds of reference material images at step ST18. Similarly, as a result of the alignment function 817 aligning the image data set of Low-kV with the image data set of High-kV, and the latter-stage data generating function 818 performing processing such as forward projection based on the image data set of Low-kV after alignment, the image reconstructing function 816 can also generate two kinds of reference material images.

The X-ray CT apparatus 10A according to the second embodiment generates a virtual projection data set to remove the effects of peristalsis of intestinal tract, respiratory movement, and body movement of a patient O, thereby enabling high-precision dual energy reconstruction based on projection data sets obtained by SDE conventional scan.

X-Ray CT Apparatus According to Third Embodiment

Since the configuration of an X-ray CT apparatus 10B according to a third embodiment is similar to that of the X-ray CT apparatus 10 shown in FIG. 1, description thereof will be omitted.

Next, the functions of the X-ray CT apparatus 10B according to the third embodiment will be described.

Figure 8:
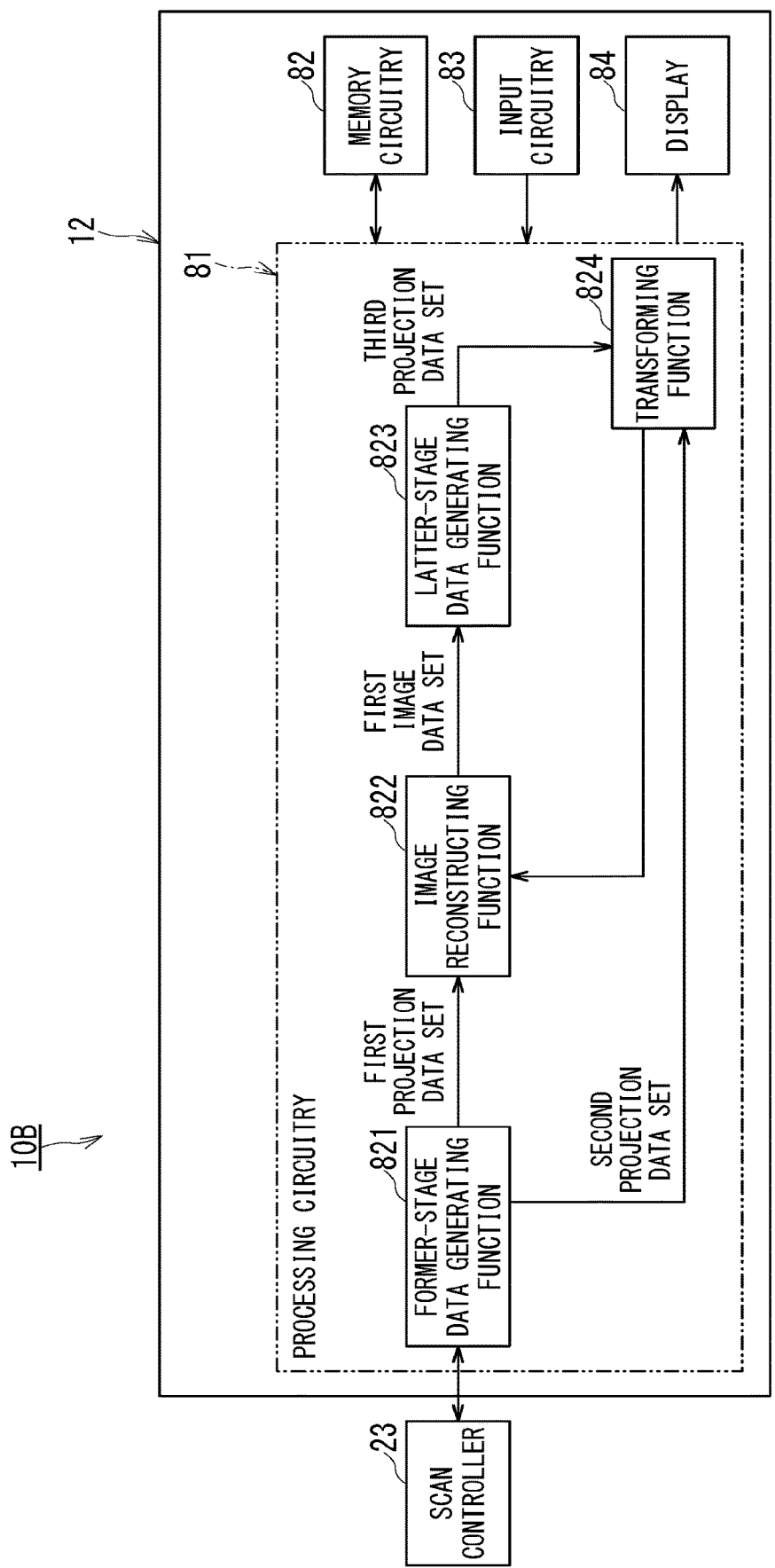
FIG. 8 is a block diagram showing functions of an X-ray CT apparatus according to a third embodiment.

FIG. 8 is a block diagram showing functions of the X-ray CT apparatus 10B according to the third embodiment.

As a result of a processing circuitry 81 of a console 12 executing a program, the X-ray CT apparatus 10B functions as a former-stage data generating function 821, an image reconstructing function 822, a latter-stage data generating function 823, and a transforming function 824. It is noted that all or some of the functions 821 to 824 may be provided as hardware in the console 12. Further, all or some of the functions 821 to 824 may be provided not only in the console 12, but also in the scan controller 23.

The functions 821 to 824 perform dual energy reconstruction based on projection data sets as in the X-ray CT apparatus 10 according to the first embodiment.

The former-stage data generating function 821 causes an imaging of a patient O to be performed separately with X-rays of a first energy and X-rays of a second energy different from the first energy during SDE helical scan by controlling the high-voltage generator 61 (shown in FIG. 1) via the scan controller 23 to switch the tube voltage to be applied to the X-ray tube 62 (shown in FIG. 1), thereby generating first and second projection data sets, respectively in a section in which mutual imaging sections are overlapped. Hereinafter, a mutually overlapping section is referred to as an "overlap section".

The former-stage data generating function 821 then causes projection data sets to be stored in the memory circuitry 82. The former-stage data generating function 821 can perform volume scan when the X-ray detector 65 (shown in FIG. 1) is a multi-slice type detector.

For example, to generate first and second projection data sets in an overlap section respectively in SDE helical scan, the former-stage data generating function 821 generates a first projection data set through movement in a positive direction (going) of the table 71 (shown in FIG. 1) and generates a second projection data set through movement in a negative direction (returning) of the table 71. FIG. 9A schematically shows helical trajectories when the first and second projection data sets are generated respectively in an overlap section by SDE helical scan.

It is noted that the X-ray CT apparatus 10B may be of two-tube type which includes two sets of X-ray tubes and X-ray detectors which are offset in the z direction in order to generate the first and second projection data sets in an overlap section, respectively. In that case, the former-stage data generating function 821 causes two-tube DE helical scan to be executed in place of SDE helical scan. That is, the former-stage data generating function 821 controls a first high-voltage generator and a second high-voltage generator via the scan controller 23 to apply a tube voltage respectively to a first X-ray tube and a second X-ray tube, thereby causing an imaging of a patient O to be separately performed with X-rays of a first energy and X-rays of a second energy different from the first energy during two-tube DE helical scan, and thereby generating first and second projection data sets respectively in the overlap section. FIG. 9B schematically shows helical trajectories when the first and second projection data sets are generated respectively in an overlap section by two-tube DE helical scan.

Each of FIGS. 9A and 9B is a side view schematically showing a helical trajectory of X-ray tube.

FIG. 9A shows a helical trajectory H1 of the X-ray tube (or the X-ray detector 65) when a first projection data set is generated by the movement in a positive direction (going) of the table 71 (shown in FIG. 1) and a helical trajectory H2 of the X-ray tube 62 (or the X-ray detector 65) when a second projection data set is generated by the movement in a negative direction (returning) of the table 71, in SDE helical scan. FIG. 9B shows a helical trajectory H1 of a first X-ray tube when the first projection data set is generated and a helical trajectory H2 of a second X-ray tube when the second projection data set is generated, in two-tube DE helical scan.

As shown in FIGS. 9A and 9B, generally, the helical trajectories are different between the first and second projection data sets generated by the former-stage data generating function 821 (shown in FIG. 8). That is, the helical trajectories are not in synchronism with each other between the first and second projection data sets. Then, in the latter-stage data generating function 823 to be described below, calculation is performed so as to bring the helical trajectory H1 of the first projection data set into synchronism with the helical trajectory H2 of the second projection data set.

Hereinafter, a case is described in which the SDE helical scan as shown in FIG. 9A is performed to generate the first and second projection data sets respectively in an overlap section.

Referring back to FIG. 8, the image reconstructing function 822 performs image reconstruction based on the first projection data set generated by the former-stage data generating function 821, thereby generating a first image data set. As the image reconstruction method, analytical methods typified by a convolution back projection (CBP) method and a filtered back projection (FBP) method, and algebraic methods are known and used.

The latter-stage data generating function 823 generates a third projection data set based on the first image data set generated by the image reconstructing function 822. The latter-stage data generating function 823 performs processing such as forward projection and processing using the Projection Slice Theorem on the first image data set to generate the third projection data set. The latter-stage data generating function 823 performs processing such as forward projection based on the first image data set such that the third projection data set in synchronism with the helical trajectory corresponding to the second projection data set is obtained.

The transforming function 824 transforms the second projection data set generated by the former-stage data generating function 821 and the third projection data set generated by the latter-stage data generating function 823 into projection data sets corresponding to reference materials.

Here, the image reconstructing function 822 performs image reconstruction based on the projection data sets after transformation by the transforming function 824, thereby generating reference-material image data sets corresponding to reference materials. The reference-material image data is also referred to as "reference-material enhanced image data".

The image reconstructing function 822 separates predetermined reference materials which are present in a target range of imaging by using the projection data sets after transformation by the transforming function 824. The image reconstructing function 822 reconstructs the reference-material image data sets for each selected reference material.

Details of the functions 821 to 824 will be described below.

FIG. 10 is a flowchart showing an operation of the X-ray CT apparatus 10B according to the third embodiment.

Here, description will be made assuming that the first projection data set and the first image data set obtained by the first tube voltage relating to the SDE helical scan are a projection data set of High-kV and an image data set of High-kV, and that the second projection data set and the second image data set obtained by the second tube voltage are a projection data set of Low-kV and image data set of Low-kV.

The former-stage data generating function 821 controls the scan controller 23 with a patient O being placed on the table 71, to cause the SDE helical scan, which is for obtaining first and second projection data sets in an overlap section, to be executed (step ST31).

The former-stage data generating function 821 acquires a raw data set of High-kV and a raw data set of Low-kV from the scan controller 23 by the SDE helical scan at step ST31 (step ST32). The former-stage data generating function 821 generates projection data sets of High-kV and Low-kV respectively from the raw data sets of High-kV and Low-kV, which are acquired at step ST32 (step ST 33).

The image reconstructing function 822 performs image reconstruction based on the projection data set of High-kV generated at step ST33, thereby generating an image data set of High-kV (step ST34).

The latter-stage data generating function 823 performs processing such as forward projection such that the projection data set of High-kV in synchronism with the helical trajectory corresponding to the projection data set of Low-kV is obtained based on the image data set of High-kV generated at step ST34, thereby generating a virtual projection data set of High-kV relating to the helical trajectory corresponding to the projection data set of Low-kV (step ST35).

The transforming function 824 performs decomposition calculation based on the virtual projection data set of High-kV in synchronism with the trajectory and generated at step ST35, and the projection data set of Low-kV, thereby calculating reference material data sets which indicate a path length of the reference material (step ST36). The image reconstructing function 822 generates reference material images from the reference material data sets generated at step ST36, and displays them on the display 84 (step ST37).

In steps ST31 to ST37, processing is carried out assuming that there are no effects of peristalsis of intestinal tract, respiratory movement, and body movement of a patient O during the SDE helical scan. The image reconstructing function 822 generates an image data set of Low-kV by performing image reconstruction based on projection data of Low-kV, and the latter-stage data generating function 823 may use, instead of the image data set of High-kV itself generated at step ST34, an image data set of High-kV after alignment with reference to the image data set of Low-kV, at step ST35. In that case, the latter-stage data generating function 823 can also mitigate the effects of peristalsis of intestinal tract, respiratory movement, and body movement of a patient O, by performing processing such as forward projection by using the image data set of High-kV after alignment.

The X-ray CT apparatus 10B according to the third embodiment makes it possible to realize high-precision dual energy reconstruction based on projection data sets obtained by SDE helical scan, which cannot be realized by conventional art. That is, the X-ray CT apparatus 10B according to the third embodiment generates a virtual projection data set in synchronism with the helical trajectory, thereby enabling high-precision dual energy reconstruction based on the projection data sets obtained by SDE helical scan.

Medical Image Processing Apparatus According to First Embodiment

FIG. 11 is a diagram showing an exemplary configuration of a medical image processing apparatus according to a first embodiment.

FIG. 11 shows a medical image processing apparatus 90 according to the first embodiment. The medical image processing apparatus 90 is, for example, a special purpose or general purpose computer. For example, functions of the medical image processing apparatus 90 may be those included in a PC (work station) for performing image processing on medical images, a medical image management apparatus (server) for storing and managing medical images, or the like.

Hereinafter, a case in which the medical image processing apparatus 90 is a special purpose or general purpose computer will be described as an example.

The medical image processing apparatus 90 includes processing circuitry 91, memory circuitry 92, input circuitry 93, and a display 94.

The processing circuitry 91 has an equivalent configuration to that of the processing circuitry 81 shown in FIG. 1. The memory circuitry 92 has an equivalent configuration to that of the memory circuitry 82 shown in FIG. 1. The input circuitry 93 has an equivalent configuration to that of the input circuitry 83 shown in FIG. 1. The display 94 has an equivalent configuration to that of the display 84 shown in FIG. 1.

Next, the functions of the medical image processing apparatus 90 according to the first embodiment will be described.

FIG. 12 is a block diagram showing functions of the medical image processing apparatus 90 according to the first embodiment.

As a result of the processing circuitry 91 executing a program, the medical image processing apparatus 90 functions as an image reconstructing function 812F, a latter-stage data generating function 813, and a transforming function 814F. It is noted that all or some of the functions 812F to 814F may be provided as hardware in the medical image processing apparatus 90.

It is noted that in FIG. 12, like elements as those shown in FIG. 3 are given like reference characters, thereby omitting description thereof.

The image reconstructing function 812F performs image reconstruction based on the first projection data set stored in the memory circuitry 92 in a similar manner as the image reconstructing function 812 (shown in FIG. 3), and thereby generates first image data set. That is, the image reconstructing function 812F performs image reconstruction based on the first projection data set selected from the first projection data set based on X-rays of a first energy and the second projection data based on X-rays of a second energy, which have been obtained by switching the tube voltage during SDE helical scan, and thereby generates a first image data set.

The transforming function 814F transforms the second projection data set stored in the memory circuitry 92 and the third projection data set generated by the latter-stage data generating function 813 into projection data set corresponding to reference materials in a similar manner as the transforming function 814 (shown in FIG. 3). Thus, the transforming function 814F transforms, in SDE helical scan, the second projection data set and the third projection data set into projection data set corresponding to reference materials, because no pair of actual measured projection data set exists at same slice center position or same z-tube position.

Since the operation of the medical image processing apparatus 90 according to the first embodiment is equivalent to that of steps ST4 to ST9 as shown in FIG. 4, description thereof will be omitted.

The medical image processing apparatus 90 according to the first embodiment makes it possible to realize high-precision dual energy reconstruction based on projection data sets obtained by SDE helical scan, which cannot be realized by conventional art. That is, the medical image processing apparatus 90 according to the first embodiment generates a virtual projection data set for a specific imaging section where a projection data set corresponding to an image data set is not existent, thereby enabling high-precision dual energy reconstruction based on the projection data set obtained by SDE helical scan.

Medical Image Processing Apparatus According to Second Embodiment

Since the configuration of a medical image processing apparatus 90A according to a second embodiment is similar to that of the medical image processing apparatus 90 shown in FIG. 11, description thereof will be omitted.

Next, the functions of the medical image processing apparatus 90A according to the second embodiment will be described.

FIG. 13 is a block diagram showing functions of the medical image processing apparatus 90A according to the second embodiment.

As a result of the processing circuitry 91 executing a program, the medical image processing apparatus 90A functions as an image reconstructing function 816F, an alignment function 817, a latter-stage data generating function 818, and a transforming function 819F. It is noted that all or some of the functions 816F to 819F may be provided as hardware in the medical image processing apparatus 90A.

Further, in FIG. 13, like elements as those shown in FIG. 6 are given like reference characters, thereby omitting description thereof.

The image reconstructing function 816F performs image reconstruction based on the first and second projection data sets stored in the memory circuitry 92 in a similar manner as the image reconstructing function 816 (shown in FIG. 6), and thereby generates first and second image data sets, respectively. That is, the image reconstructing function 816F performs image reconstruction respectively based on the first projection data set based on X-rays of a first energy and the second projection data set based on X-rays of a second energy, which have been obtained by switching the tube voltage during SDE conventional scan, and thereby generates first and second image data sets.

The transforming function 819F transforms the second projection data set stored in the memory circuitry 92, and the third projection data set generated by the latter-stage data generating function 818 into projection data sets corresponding to reference materials in a similar manner as the transforming function 819 (shown in FIG. 6).

Since the operation of the medical image processing apparatus 90A according to the second embodiment is equivalent to that of steps ST14 to ST18 as shown in FIG. 7, description thereof will be omitted.

The medical image processing apparatus 90A according to the second embodiment generates a virtual projection data set to remove the effects of peristalsis of intestinal tract, respiratory movement, and body movement of a patient O, thereby enabling high-precision dual energy reconstruction based on projection data sets obtained by SDE conventional scan.

Medical Image Processing Apparatus According to Third Embodiment

Since the configuration of a medical image processing apparatus 90B according to a third embodiment is similar to that of the medical image processing apparatus 90 shown in FIG. 11, description thereof will be omitted.

Next, the functions of the medical image processing apparatus 90B according to the third embodiment will be described.

FIG. 14 is a block diagram showing functions of the medical image processing apparatus 90B according to the third embodiment.

As a result of the processing circuitry 91 executing a program, the medical image processing apparatus 90B functions as an image reconstructing function 822F, a latter-stage data generating function 823, and a transforming function 824F. It is noted that all or some of the functions 822F to 824F may be provided as hardware in the medical image processing apparatus 90B.

Further, in FIG. 14, like elements as those shown in FIG. 8 are given like reference characters, thereby omitting description thereof.

The image reconstructing function 822F performs image reconstruction based on the first projection data set stored in the memory circuitry 92 in a similar manner as the image reconstructing function 822 (shown in FIG. 8), and thereby generates a first image data set. That is, the image reconstructing function 822F performs image reconstruction based on the first projection data set based on X-rays of a first energy which has been obtained by switching the tube voltage during SDE helical scan, and thereby generates a first image data set.

The transforming function 824F transforms the second projection data set, and the third projection data set, which is generated by the latter-stage data generating function 823, into projection data sets corresponding to reference materials in a similar manner as the transforming function 834 (shown in FIG. 8).

Since the operation of the medical image processing apparatus 90B according to the third embodiment is equivalent to that of steps ST31 to ST37 as shown in FIG. 10, description thereof will be omitted.

The medical image processing apparatus 90B according to the third embodiment makes it possible to realize high-precision dual energy reconstruction based on projection data set obtained by SDE helical scan, which cannot be realized by conventional art. That is, the medical image processing apparatus 90B according to the third embodiment generates a virtual projection data set in synchronism with the helical trajectory, thereby enabling high-precision dual energy reconstruction based on the projection data sets obtained by SDE helical scan.

The X-ray CT apparatus and the medical image processing apparatus according to at least one of the embodiments described above enables high-precision dual energy reconstruction based on the projection data.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray CT apparatus, comprising:
an X-ray tube configured to radiate X-rays;
a voltage generator configured to apply voltage to the X-ray tube;
an X-ray detector configured to detect the X-rays; and
processing circuitry configured to,
control the voltage generator during helical scan to switch tube voltage to be applied to the X-ray tube, thereby causing an imaging to be performed separately with X-rays of a first energy and X-rays of a second energy different from the first energy, and generating first and second projection data sets of different imaging sections, respectively,
perform image reconstruction based on the first projection data set, thereby generating a first image,
generate a third projection data set based on the first image,
perform transformation processing to transform the second and third projection data sets into projection data sets corresponding to reference materials, and
perform image reconstruction based on the projection data set after the transformation processing, thereby generating reference material images corresponding to reference materials.

2. The X-ray CT apparatus according to claim 1, wherein the processing circuitry is configured to perform forward projection on the first image, thereby generating the third projection data set.

3. The X-ray CT apparatus according to claim 1, wherein the processing circuitry is configured to:
perform forward projection on a portion of the first image, the portion corresponding to a section being same as a imaging section corresponding to the second projection data set; and
use a portion of the third projection data set, the portion corresponding to a section being same as the imaging section corresponding to the second projection data set.

4. The X-ray CT apparatus according to claim 1, wherein the processing circuitry is configured to:
perform image reconstruction based on the second projection data set, thereby generating a second image;
perform forward projection on the second image, thereby generating a fourth projection data set;

perform transformation processing to transform the first and fourth projection data sets into projection data set corresponding to reference materials;

perform image reconstruction based on two projection data sets after the transformation processing, thereby generating two reference material images; and take an average of corresponding kinds of images of the two sets of reference material images, thereby generating two kinds of reference material images.

5. The X-ray CT apparatus according to claim 1, wherein the processing circuitry is configured to:

perform at least one of control to make a rotational speed of the X-ray tube and the X-ray detector during the helical scan not less than a threshold, and control to make a feed speed of the object during the helical scan not more than a threshold.

6. The X-ray CT apparatus according to claim 1, wherein the processing circuitry is configured to:

perform image reconstruction based on the second projection data set, thereby generating a second image; and perform forward projection by using, in place of the first image, a first image after alignment with reference to the second image data set, thereby generating the third projection data set.

7. The X-ray CT apparatus according to claim 1, wherein the X-ray detector is a detector of two-dimensional array type, and the processing circuitry is configured to cause the imaging to be performed by volume scan.

* * * * *